US008097413B2

(12) United States Patent
Uhl et al.

(10) Patent No.: US 8,097,413 B2
(45) Date of Patent: *Jan. 17, 2012

(54) **DETECTION OF GROUP B *STREPTOCOCCUS***

(75) Inventors: James R Uhl, Rochester, MN (US); Franklin R Cockerill, III, Rochester, MN (US); Christian Aichinger, Munich (DE); Astrid Reiser, Antdorf (DE)

(73) Assignees: Mayo Foundation for Medical Education and Research, Rochester, MN (US); Roche Molecular Systems, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/843,380

(22) Filed: Jul. 26, 2010

(65) Prior Publication Data

US 2010/0291582 A1 Nov. 18, 2010

Related U.S. Application Data

(60) Continuation of application No. 12/235,898, filed on Sep. 23, 2008, now Pat. No. 7,790,875, which is a division of application No. 10/716,005, filed on Nov. 18, 2003, now Pat. No. 7,427,475.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........ 435/6.1; 435/91.1; 536/23.1; 536/24.3

(58) Field of Classification Search ........................ None
See application file for complete search history.

(56) References Cited

U.S. PATENT DOCUMENTS

| 5,035,996 | A | | 7/1991 | Hartley |
| 5,538,848 | A | * | 7/1996 | Livak et al. ........................ 435/6 |
| 5,541,308 | A | | 7/1996 | Hogan et al. |
| 5,702,895 | A | | 12/1997 | Matsunaga et al. |
| 5,837,452 | A | | 11/1998 | Clark et al. |
| 5,925,517 | A | | 7/1999 | Tyagi et al. |
| 6,140,054 | A | | 10/2000 | Wittwer et al. |
| 6,174,670 | B1 | | 1/2001 | Wittwer et al. |
| 6,245,514 | B1 | | 6/2001 | Wittwer |
| 6,593,093 | B1 | | 7/2003 | Uhl et al. |

FOREIGN PATENT DOCUMENTS

| EP | 0 269 764 | | 6/1988 |
| EP | 0 338 591 | | 10/1989 |
| EP | 0 526 876 | | 2/1993 |
| EP | 1 045 033 | | 10/2000 |
| EP | 1 160 333 | | 12/2001 |
| WO | WO 98/48046 | * | 10/1998 |
| WO | WO 99/19466 | | 4/1999 |
| WO | WO 99/45155 | | 9/1999 |
| WO | WO 00/37646 | | 6/2000 |
| WO | WO 00/70096 | | 11/2000 |
| WO | WO 01/12803 | | 2/2001 |
| WO | WO 01/23604 | | 4/2001 |
| WO | WO 02/18660 | | 3/2002 |
| WO | WO 02/34771 | | 5/2002 |
| WO | WO 02/061390 | | 8/2002 |
| WO | WO 02/092818 | | 11/2002 |
| WO | WO 03/025216 | | 3/2003 |
| WO | WO 03/068918 | | 8/2003 |
| WO | WO 03/093306 | | 11/2003 |

OTHER PUBLICATIONS

Belanger et al; Journal of Clinical Microbiology, vol. 40, pp. 1436-1440, Apr. 2002.*
Genbank Accession No. NC_004368, dated Nov. 15, 2002, 5 pages.
"LightCycler-FastStart DNA Master Hybridization Probes," 1999 Roche Diagnostics GmbH Technical Manual, retrieved from the internet on Feb. 6, 2004: http://www.roche-applied-science.com.
Abd-Elsalam, "Bioinformatic Tools and Guideline for PCR Primer Design," *African J. Biotech.*, 2003, 2:91-95.
Ahern, "Biochemical, Reagent Kits Offer Scientists Good Return On Investment," *The Scientist*, 1995, 9:20-24.
Al-Robaiy et al., "Rapid Competitive PCR Using Melting Curve Analysis for DNA Quantification," *BioTechniques*, 2001, 31:1382-1388.
Arthur et al., "*Enterococcus faecium* transposon Tn1546 transposase, resolvase, vanR, vanS, vanH, vanA, vanX, vanY and teicoplanin resistance protein (vanZ) genes, complete cds," 1993, database accession No. M97297.
Ballard et al., "Comparison of three PCR primer sets for identification of vanB gene carriage in feces and correlation with carriage of vancomycin-resistant enterococci: interference by vanB-containing anaerobic bacilli," *Antimicrob._Agents*13 *Chemother.*, 2005, 49:77-81.
Bassler et al., "Use of a Fluorogenic Probe in a PCR-Based Assay for the Detection of *Listeria monocytogenes*," *Applied and Environmental Microbiology*, 1995, 61(10):3724-3728.
Beards et al., "Investigation of Vesicular Rashes for HSV and VZV by PCR," *J. Med. Virol.*, 1998, 54:155-157.
Belanger et al., "Rapid Detection of Shiga Toxin-Producing Bacteria in Feces by Multiplex PCR with Molecular Beacons on the Smart Cycler," *Journal of Clinical Microbiology*, 2002, 40:1436-1440.
Bélanger et al., "Rapid Detection of Shiga Toxin-Producing Bacteria in Feces by Multiplex PCR with Molecular Beacons on the Smart Cycler," *J. Clin. Microbiol.*, 2002, 40:1436-1440.
Bellin et al "Rapid Detection of Enterohemorrhagic *Escherichia coli* by Real-Time PCR with Fluorescent Hybridization Probes," *Journal of Clinical Microbiology* 2001, 39:370-374.

(Continued)

*Primary Examiner* — Jehanne Sitton
(74) *Attorney, Agent, or Firm* — Fish & Richardson P.C.

(57) ABSTRACT

The invention provides methods to detect group B *streptococcus* (GBS) in biological samples using real-time PCR. Primers and probes for the detection of GBS are provided by the invention. Articles of manufacture containing such primers and probes for detecting GBS are further provided by the invention.

14 Claims, No Drawings

OTHER PUBLICATIONS

Bellin et al., "Rapid Detection of Enterohemorrhagic *Escherichia coli* by Real-Time PCR with Fluorescent Hybridization Probes," *J. Clin. Microbiol.*, 2001, 39:370-374.

Bergeron et al, "Rapid Detection of Group B Streptococci in Pregnant Women at Delivery," *New England Journal of Medicine*, 2000, 343:175-179.

Bergeron et al., "Rapid Detection of Group B Streptococci in Pregnant Women at Delivery," *New England J. Med.*, 2000, 343(3):175-179.

Brink et al., "Nucleic Acid Sequence-Based Amplification, A New Method for Analysis of Spliced and Unspliced Epstein-Barr Virus Latent Transcripts, and Its Comparison with Reverse Transcriptase PCR," *J. Clin. Microbiol.*, 1998, 36(11):3164-3169.

Buck et al., "Design Strategies and Performance of Custom DNA Sequencing Primers," *BioTechniques*, 1999, 27(3):528-536.

Caplin et al., "LightCycler™ hybridization probes; The most direct way to monitor PCR amplification for quantification and mutation detection," *Biochemica*, 1999, 1:5-8.

Chen et al., An Automated Fluorescent PCR Method for Detection of Shiga Toxin-Producing *Escherichia coli* in Foods,: *Appl. Environ. Microbiol.*, 1998, 64:4210-4216.

Csordas et al., "Comparison of primers for the detection of *Salmonella enterica* serovars using real-time PCR," *Lett. Appl. Microbiol.*, 2004, 39:187-193.

Davison and Scott, "The Complete DNA Sequence of Varicella-Zoster Virus." *J. Gen. Virol.*, 1986, 67:1759-1816.

Didenko, "DNA Probes Using Fluorescence Resonance Energy Transfer (FRET): Designs and Applications," *BioTechniques*, 2001, 31:1106-1121.

Elnifro et al., "Multiplex PCR: optimization and application in diagnostic virology," *Clin. Microbiol. Rev.*, 2000, 13:559-570.

Espy et al., "Detection of Smallpox Virus DNA by LightCycler PCR," *J. Clin. Microbiol.*, 2002, 40(6):1985-1988.

Espy et al., "Diagnosis of Herpes Simplex Virus Infections in the Clinical Laboratory by LightCycler PCR," *J. Clin. Microbiol.*, 2000, 38(2):795-799.

Espy et al., "Diagnosis of Varicella-Zoster Virus Infections in the Clinical Laboratory by LightCycler PCR," *J. Clin. Microbiol.*, 2000, 38(9):3187-3189.

Espy et al., "Quantification of Epstein-Barr Virus (EBV) Viral Load in Transplant Patients by LightCycler PCR," *Abstracts of the General Meeting of the American Society for Microbiology*, 101st General Meeting, May 20-24, 2001, 101:182, Abstract No. C-148.

Grisold et al., "Detection of Methicillin-Resistant *Staphylococcus aureus* and Simultaneous Confirmation by Automated Nucleic Acid Extraction and Real-Time PCR," *J. Clin. Microbiol.*, 2002, 40:2392-2397.

Holland et al., "PCR Detection of *Escherichia coli* O157:H7 Directly from Stools: Evaluation of Commercial Extraction Methods for Purifying Fecal DNA," *J. Clin. Microbiol.*, 2000, 38:4108-4113.

Huletsky et al., "Rapid Detection of Vancomycin-Resistant Enterococci Directly from Rectal Swabs by Real-Time PCR Using the Smart Cycler," *Abstracts of the Interscience Conference on Antimicrobial Agents and Chemotherapy*, Chicago, Illinois, Sep. 22-25, 2001, 41:409 (Abstract K-1195).

Ito et al., "*Staphylococcus aureus* DNA, type-I staphylococcal cassette chromosome mec," 1999, database accession No. AB033763.

Ke et al., "Development of conventional and real-time PCR assays for the rapid detection of group B streptococci," *Clin. Chem.*, 2000, 46(3):324-331.

Kinoshita et al., "Variation of R1 Repeated Sequence Present in Open Reading Frame 11 of Varicella-Zoster Virus Strains," *J. Virol.*, 1988, 62(3):1097-1100.

Livak et al., "Oligonucleotides with Fluorescent Dyes at Opposite Ends Provide A Quenched Probe System Useful for Detecting PCR Product and Nucleic Acid Hybridization," *Genome Research*, 1995, 4:357-362.

Lowe et al., "A computer program for selection of oligonucleotide primers for polymerase chain reactions," *Nucl. Acids Res.*, 1990, 18(7):1757-1761.

Machiels et al., "New Protocol for DNA Extraction of Stool," *BioTechniques*, 2000, 28:286-290.

McOrist et al., "A comparison of five methods for extraction of bacterial DNA from human faecal samples," *J. Microbiol. Meth.*, 2002, 50:131-139.

Palladino et al., "Rapid Detection of *vanA* and *vanB* Genes Directly from Clinical Specimens and Enrichment Broths by Real-Time Multiplex PCR Assay," *J. Clin. Microbiol.*, 2003, 41:2483-2486.

Palladino et al., "Real-time PCR for the rapid detection of *vanA* and *vanB* genes," *Diagnostic Microbiology and Infectious Disease*, 2003, 45:81-84.

Patel et al., "*Enterococcus faecalis* vancomycin resistance protein vanB gene, partial cds," 1997, database accession No. U72704.

Patel et al., "*Enterococcus faecium* vancomycin resistance protein B (vanB) gene, partial cds," 1997, database accession No. U94528.

Petrich et al., "Direct detection of *vanA* and *vanB* genes in clinical specimens for rapid identification of vancomycin resistant enterococci (VRE) using multiplex PCR," *Molecular and Cellular Probes*, 1999, 13:275-281.

Ramotar et al., "Direct Detection of Verotoxin-Producing *Escherichia coli* in Stool Samples by PCR," *J. Clin. Microbiol.*, 1995, 33:519-524.

Reischl et al., "Rapid Identification of Methicillin-Resistant *Staphylococcus aureus* and Simultaneous Species Confirmation Using Real-Time Fluorescence PCR," *J. Clin. Microbiol.*, 2000, 38:2429-2433.

Ryncarz et al., "Development of a High-Throughput Quantitative Assay for Detecting Herpes Simplex Virus DNA in Clinical Samples," *J. Clin. Microbiol.*, 1999, 37:1941-1947.

Sample et al., "Two Related Epstein-Barr Virus Membrane Proteins are Encoded by Separate Genes," *J. Virol.*, 1989, 63(2):933-937.

Sloan et al., "Evaluation of a Combined LightCycler Assay for the Detection of VANA, VANB, and VANB-2/3 Genes in Enterococci," *Abstracts of the General Meeting of the American Society for Microbiology*, 2002, 102:143 (Abstract C-242).

Smith, "Application of Lightcycler Real Time PCR in Clinical Virology," *Clin. Chem. Lab. Med.*, 2001, Special Supplement, 39:S60, Abstract No. ISW14-2.

Telenti et al., "Detection of Epstein-Barr Virus by Polymerase Chain Reaction," *J. Clin. Microbiol.*, 1990, 28(10):2187-2190.

Tettelin et al, "Complete genome sequence and comparative genomic analysis of an emerging human pathogen, serotype V *Streptococcus agalactiae*," *PNAS*, 2002, 99:12391-12396.

Tichopad et al , "Inhibition of real-time RT-PCR quantification due to tissue-specific contaminants," *Mol. Cell. Probes*, 2004, 18:45-50.

Van Der Hoek et al., "Isolation of Human Immunodeficiency Virus Type 1 (HIV-1) RNA from Feces by a Simple Method and Difference between HIV-1 Subpopulations in Feces and Serum," *J. Clin. Microbiol.*, 1995, 33:581-588.

\* cited by examiner

DETECTION OF GROUP B *STREPTOCOCCUS*

CROSS REFERENCE TO RELATED APPLICATIONS

This application is a Continuation application and claims the benefit of priority under 35 U.S.C. §120 of U.S. application Ser. No. 12/235,898 filed on Sep. 23, 2008, now allowed, which is a Divisional application and claims the benefit of priority under 35 U.S.C. §121 of U.S. application Ser. No. 10/716,005 filed on Nov. 18, 2003, now issued as U.S. Pat. No. 7,427,475.

TECHNICAL FIELD

This invention relates to bacterial diagnostics, and more particularly to detection of group B *streptococcus* (GBS).

BACKGROUND

Group B *Streptococcus* (GBS) is a Gram positive bacteria commonly found in the throat and lower intestine of adults, and in the vagina of women. Normally, this organism does not cause disease in the host. During childbirth, however, an infant can become infected with GBS. GBS infections are the leading cause of neonatal morbidity and mortality in the United States, with fatality ratios as high as 50% in untreated cases. In recent years, antibiotics administered during labor have greatly reduced the incidence of neonatal GBS.

Current CDC recommendations call for screening of women for GBS during week 35 to 37 weeks' gestation by culture. Women found to be colonized with GBS are treated with intravenous antibiotics during labor. This approach has reduced the incidence of neonatal infection and fewer patients are provided unnecessary antibiotic treatment. However, the problem of GBS neonatal sepsis has not been eliminated. Colonization with GBS is often transient, so lack of colonization at 35 weeks gestation does not guarantee that there will be no GBS present at week 40. Also, many patients present to healthcare providers first at the time of labor and have not been screened for GBS. The decision to treat with antibiotics in these cases must be made on the basis of risk factors such as gestation<37 weeks, membrane rupture>12 hours, young maternal age, and/or black or Hispanic ethnicity.

Ideally, the determination of GBS colonization would be made during early labor and the laboratory results available within a few hours. Conventional identification of GBS requires culture. As culture may require up to 72 hours for a definitive answer, physicians may provide unnecessary antimicrobics at the time of delivery on an empiric basis. Overuse of antimicrobics may predispose to the development of antimicrobial resistance and add to the risk of adverse reactions including life-threatening anaphylaxis. Rapid antigen tests (e.g., latex agglutination) also have been used to diagnose GBS, but these tests lack sensitivity when compared to culture. In fact, the sensitivities of antigen tests for detecting GBS are so low that the FDA has issued an alert that these types of assays cannot be used to diagnose GBS without culture backup.

SUMMARY

The invention provides for methods of identifying group B *streptococcus* (GBS) in a biological sample or in a non-biological sample. Primers and probes for detecting GBS are provided by the invention, as are kits containing such primers and probes. Methods of the invention can be used to rapidly identify GBS DNA from specimens for diagnosis of GBS infection. Using specific primers and probes, the methods include amplifying and monitoring the development of specific amplification products using fluorescence resonance energy transfer (FRET).

In one aspect of the invention, there is provided a method for detecting the presence or absence of GBS in a biological sample from an individual or in a non-biological sample. The method to detect GBS includes performing at least one cycling step, which includes an amplifying step and a hybridizing step. The amplifying step includes contacting the sample with a pair of pts primers to produce a pts amplification product if a GBS pts nucleic acid molecule is present in the sample. The hybridizing step includes contacting the sample with a pair of pts probes. Generally, the members of the pair of pts probes hybridize within no more than five nucleotides of each other. A first pts probe of the pair of pts probes is typically labeled with a donor fluorescent moiety and a second pts probe of the pair of pts probes is labeled with a corresponding acceptor fluorescent moiety. The method further includes detecting the presence or absence of FRET between the donor fluorescent moiety of the first pts probe and the acceptor fluorescent moiety of the second pts probe. The presence of FRET is usually indicative of the presence of GBS in the sample, while the absence of FRET is usually indicative of the absence of GBS in the sample.

A pair of pts primers generally includes a first pts primer and a second pts primer. The first pts primer can include the sequence 5'-TGA GAA GGC AGT AGA AAG CTT AG-3' (SEQ ID NO:1), and the second pts primer can include the sequence 5'-TGC ATG TAT GGG TTA TCT TCC-3' (SEQ ID NO:2). A first pts probe can include the sequence 5'-CAA ATT AAA GAG ACT ATT CGT GCA A-3' (SEQ ID NO:3), and the second pts probe can include the sequence 5'-CAA GTA AAT GCA GAA ACA GG-3' (SEQ ID NO:4).

In some aspects, one of the pts primers can be labeled with a fluorescent moiety (either a donor or acceptor, as appropriate) and can take the place of one of the pts probes.

The members of the pair of pts probes can hybridize within no more than two nucleotides of each other, or can hybridize within no more than one nucleotide of each other. A representative donor fluorescent moiety is fluorescein, and corresponding acceptor fluorescent moieties include LC-Red 640, LC-Red 705, Cy5, and Cy5.5. Additional corresponding donor and acceptor fluorescent moieties are known in the art.

In one aspect, the detecting step includes exciting the sample at a wavelength absorbed by the donor fluorescent moiety and visualizing and/or measuring the wavelength emitted by the acceptor fluorescent moiety (i.e., visualizing and'/or measuring FRET). In another aspect, the detecting step includes quantitating the FRET. In yet another aspect, the detecting step can be performed after each cycling step (e.g., in real-time).

Generally, the presence of FRET within 45 cycles (e.g., 20, 25, 30, 35, or 40 cycles) indicates the presence of a GBS infection in the individual. In addition, determining the melting temperature between one or both of the pts probe(s) and the pts amplification product can confirm the presence or absence of the GBS.

Representative biological sample include anal and/or vaginal swabs. The above-described methods can further include preventing amplification of a contaminant nucleic acid. Preventing amplification can include performing the amplifying step in the presence of uracil and treating the sample with uracil-DNA glycosylase prior to amplifying.

In addition, the cycling step can be performed on a control sample. A control sample can include the same portion of the GBS pts nucleic acid molecule. Alternatively, a control sample can include a nucleic acid molecule other than a GBS pts nucleic acid molecule. Cycling steps can be performed on such a control sample using a pair of control primers and a pair of control probes. The control primers and probes are other than pts primers and probes. One or more amplifying steps produces a control amplification product. Each of the control probes hybridizes to the control amplification product.

In another aspect of the invention, there are provided articles of manufacture, or kits. Kits of the invention can include a pair of pts primers, and a pair of pts probes, and a donor and corresponding acceptor fluorescent moieties. For example, the first pts primer provided in a kit of the invention can have the sequence 5'-TGA GAA GGC AGT AGA AAG CTT AG-3' (SEQ ID NO:1) and the second pts primer can have the sequence 5'-TGC ATG TAT GGG TTA TCT TCC-3' (SEQ ID NO:2). The first pts probe provided in a kit of the invention can have the sequence 5'-CAA ATT AAA GAG ACT ATT CGT GCA A-3' (SEQ ID NO:3) and the second pts probe can have the sequence 5'-CAA GTA AAT GCA GAA ACA GG-3' (SEQ ID NO:4).

Articles of manufacture can include fluorophoric moieties for labeling the probes or probes already labeled with donor and corresponding acceptor fluorescent moieties. The article of manufacture can also include a package insert having instructions thereon for using the primers, probes, and fluorophoric moieties to detect the presence or absence of GBS in a sample.

In yet another aspect of the invention, there is provided a method for detecting the presence or absence of GBS in a biological sample from an individual or in a non-biological sample. Such a method includes performing at least one cycling step. A cycling step can include an amplifying step and a hybridizing step. Generally, an amplifying step includes contacting the sample with a pair of pts primers to produce a pts amplification product if a GBS pts nucleic acid molecule is present in the sample. Generally, a hybridizing step includes contacting the sample with a pts probe. Such a pts probe is usually labeled with a donor fluorescent moiety and a corresponding acceptor fluorescent moiety. The method further includes detecting the presence or absence of fluorescence resonance energy transfer (FRET) between the donor fluorescent moiety and the acceptor fluorescent moiety of the pts probe. The presence or absence of fluorescence is indicative of the presence or absence of GBS in said sample.

In one aspect, amplification can employ a polymerase enzyme having 5' to 3' exonuclease activity. Thus, the first and second fluorescent moieties would be within no more than 5 nucleotides of each other along the length of the probe. In another aspect, the pts probe includes a nucleic acid sequence that permits secondary structure formation. Such secondary structure formation generally results in spatial proximity between the first and second fluorescent moiety. According to this method, the second fluorescent moiety on a probe can be a quencher.

In another aspect of the invention, there is provided a method for detecting the presence or absence of GBS in a biological sample from an individual or in a non-biological sample. Such a method includes performing at least one cycling step. A cycling step can include an amplifying step and a dye-binding step. An amplifying step generally includes contacting the sample with a pair of pts primers to produce a pts amplification product if a GBS pts nucleic acid molecule is present in the sample. A dye-binding step generally includes contacting the pts amplification product with a double-stranded DNA binding dye. The method further includes detecting the presence or absence of binding of the double-stranded DNA binding dye into the amplification product. According to the invention, the presence of binding is typically indicative of the presence of GBS in the sample, and the absence of binding is typically indicative of the absence of GBS in the sample. Such a method can further include the steps of determining the melting temperature between the pts amplification product and the double-stranded DNA binding dye. Generally, the melting temperature confirms the presence or absence of GBS. Representative double-stranded DNA binding dyes include SYBRGreenI®, SYBRGold®, and ethidium bromide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

A real-time assay for detecting GBS in a biological sample or in a non-biological sample that is more sensitive and specific than existing assays is described herein. Primers and probes for detecting GBS infections and articles of manufacture containing such primers and probes are provided by the invention. The increased sensitivity of real-time PCR for detection of GBS compared to other methods, as well as the improved features of real-time PCR including sample containment and real-time detection of the amplified product, make feasible the implementation of this technology for routine diagnosis of GBS infections in the clinical laboratory.

GBS Nucleic Acids and Oligonucleotides

The invention provides methods to detect GBS by amplifying, for example, a portion of the GBS pts nucleic acid. GBS nucleic acids other than those exemplified herein (e.g., other than pts) also can be used to detect GBS in a sample and are known to those of skill in the art. Nucleic acid sequences from GBS are available (see, for example, GenBank Accession Nos. NC_004368 and NC_004116). Specifically, primers and probes to amplify and detect GBS pts nucleic acid molecules are provided by the invention.

Primers that amplify a GBS nucleic acid molecule, e.g., GBS pts can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 30 nucleotides in length.

Designing oligonucleotides to be used as hybridization probes can be performed in a manner similar to the design of primers, although the members of a pair of probes preferably anneal to an amplification product within no more than 5 nucleotides of each other on the same strand such that FRET can occur (e.g., within no more than 1, 2, 3, or 4 nucleotides of each other). This minimal degree of separation typically brings the respective fluorescent moieties into sufficient proximity such that FRET occurs. It is to be understood, however, that other separation distances (e.g., 6 or more nucleotides) are possible provided the fluorescent moieties are appropriately positioned relative to each other (for example, with a linker arm) such that FRET can occur. In addition, probes can be designed to hybridize to targets that contain a polymorphism or mutation, thereby allowing differential detection of GBS strains based on either absolute hybridization of different pairs of probes corresponding to the particular GBS strain to be distinguished or differential melting temperatures between, for example, members of a pair of probes and each amplification product corresponding to a GBS strain to be distinguished. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 30 nucleotides in length.

Constructs of the invention include vectors containing a GBS nucleic acid molecule, e.g., GBS pts or a fragment thereof. Constructs of the invention can be used, for example, as control template nucleic acid molecules. Vectors suitable for use in the present invention are commercially available and/or produced by recombinant DNA technology methods routine in the art. GBS pts nucleic acid molecules can be obtained, for example, by chemical synthesis, direct cloning from GBS, or by PCR amplification. A GBS nucleic acid molecule or fragment thereof can be operably linked to a promoter or other regulatory element such as an enhancer sequence, a response element, or an inducible element that modulates expression of the GBS nucleic acid molecule. As used herein, operably linking refers to connecting a promoter and/or other regulatory elements to a GBS nucleic acid molecule in such a way as to permit and/or regulate expression of the GBS nucleic acid molecule. A promoter that does not normally direct expression of GBS pts can be used to direct transcription of a pts nucleic acid using, for example, a viral polymerase, a bacterial polymerase, or a eukaryotic RNA polymerase II. Alternatively, the pts native promoter can be used to direct transcription of a pts nucleic acid. In addition, operably linked can refer to an appropriate connection between a GBS pts promoter or regulatory element and a heterologous coding sequence (i.e., a non-pts coding sequence, for example, a reporter gene) in such a way as to permit expression of the heterologous coding sequence.

Constructs suitable for use in the methods of the invention typically include, in addition to GBS pts nucleic acid molecules, sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing GBS pts nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens* and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the present invention include oligonucleotides capable of acting as a point of initiation of nucleic acid synthesis within GBS pts nucleic acid sequences. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T lacteus, T. rubens, Bacillus stearothermophilus*, and *Methanothermus fervidus*. Nonetheless, polymerases that are not thermostable also can be employed in PCR assays provided the enzyme is replenished.

If the GBS template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min.

If the double-stranded nucleic acid is denatured by heat, the reaction mixture is allowed to cool to a temperature that promotes annealing of each primer to its target sequence on the GBS nucleic acid. The temperature for annealing is usually from about 35° C. to about 65° C. Annealing times can be from about 10 secs to about 1 min. The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° to 80° C.). Extension times can be from about 10 secs to about 5 mins.

PCR assays can employ GBS nucleic acid such as DNA or RNA, including messenger RNA (mRNA). The template nucleic acid need not be purified; it may be a minor fraction of a complex mixture, such as GBS nucleic acid contained in human cells. DNA or RNA may be extracted from a biological sample such as an anal and/or vaginal swab by routine techniques such as those described in *Diagnostic Molecular Microbiology: Principles and Applications* (Persing et al. (eds), 1993, American Society for Microbiology, Wash. D.C.). Nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 μg denatured template DNA, 50 pmoles of each oligonucleotide primer, 2.5 U of Taq polymerase, and 10% DMSO). The reactions usually contain 150 to 320 μM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target GBS nucleic acid molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor and a corresponding acceptor fluorescent moiety are positioned within a certain distance of each other, energy transfer takes place between the two fluorescent moieties that can be visualized or otherwise detected and/or quantitated. Two oligonucleotide probes, each containing a fluorescent moiety, can hybridize to an amplification product at particular positions determined by the complementarity of the oligonucleotide probes to the GBS target nucleic acid sequence. Upon hybridization of the oligonucleotide probes to the amplification product nucleic acid at the appropriate positions, a FRET signal is generated. Hybridization temperatures can range from about 35 to about 65° C. for about 10 secs to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC™-Red 640, LC™-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as an LC™-Red 640-NHS-ester can be combined with C6-Phosphoramidites (available from ABI (Foster City, Calif.) or Glen Research (Sterling, Va.)) to produce, for example, LC™-Red 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPG's that require coupling of a fluorescein-NHS-ester after oligonucleotide synthesis.

Detection of Group B *Streptococcus*

The presence of GBS has been detected by culturing the organism as well as rapid antigen tests. Conventional PCR methods also have been used to detect GBS. Conventional PCR-based amplification is generally followed by transfer of the amplification products to a solid support and detection using a labeled probe (e.g., a Southern or Northern blot). These methods are labor intensive and frequently require more than one day to complete. Additionally, the manipulation of amplification products for the purpose of detection (e.g., by blotting) increases the risk of carry-over contamination and false positives.

By using commercially available real-time PCR instrumentation (e.g., LightCycler™, Roche Molecular Biochemicals, Indianapolis, Ind.), PCR amplification and detection of the amplification product can be combined in a single closed cuvette with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

The present invention provides methods for detecting the presence or absence of GBS in a biological sample from an individual or in a non-biological sample. Methods provided by the invention avoid problems of sample contamination, false negatives, and false positives. The methods include performing at least one cycling step that includes amplifying a GBS portion of a pts nucleic acid molecule from a sample using a pair of pts primers. Each of the pts primers anneals to a target within or adjacent to a GBS pts nucleic acid molecule such that at least a portion of each amplification product contains nucleic acid sequence corresponding to pts. More importantly, the amplification product should contain the nucleic acid sequences that are complementary to the pts probes. The pts amplification product is produced provided that GBS nucleic acid is present. Each cycling step further includes contacting the sample with a pair of pts probes. According to the invention, one member of each pair of the pts probes is labeled with a donor fluorescent moiety and the other is labeled with a corresponding acceptor fluorescent moiety. The presence or absence of FRET between the donor fluorescent moiety of the first pts probe and the corresponding acceptor fluorescent moiety of the second pts probe is detected upon hybridization of the pts probes to the pts amplification product.

Each cycling step includes an amplification step and a hybridization step, and each cycling step is usually followed by a FRET detecting step. Multiple cycling steps are performed, preferably in a thermocycler. Methods of the invention can be performed using the pts primer and probe set to detect the presence of GBS. Detection of FRET in the pts reaction indicates the presence of a GBS.

As used herein, "amplifying" refers to the process of synthesizing nucleic acid molecules that are complementary to one or both strands of a template nucleic acid molecule (e.g., GBS pts nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

If amplification of GBS nucleic acid occurs and an amplification product is produced, the step of hybridizing results in a detectable signal based upon FRET between the members of the pair of probes. As used herein, "hybridizing" refers to the annealing of probes to an amplification product. Hybridization conditions typically include a temperature that is below the melting temperature of the probes but that avoids non-specific hybridization of the probes.

Generally, the presence of FRET indicates the presence of GBS in the sample, and the absence of FRET indicates the absence of GBS in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within 45 cycling steps is indicative of a GBS infection.

Methods of the invention also can be used for GBS vaccine efficacy studies or epidemiology studies. For example, an attenuated GBS in an anthrax vaccine can be detected using the methods of the invention during the time when bacteria is still present in an individual. For such vaccine efficacy studies, the methods of the invention can be used to determine, for example, the persistence of an attenuated strain of GBS used in a vaccine, or can be performed in conjunction with an additional assay such as a serologic assay to monitor an individual's immune response to such a vaccine. In addition, methods of the invention can be used to distinguish one GBS strain from another for epidemiology studies of, for example, the origin or severity of an outbreak of GBS.

Representative biological samples that can be used in practicing the methods of the invention include dermal swabs, cerebrospinal fluid, blood, sputum, bronchio-alveolar lavage, bronchial aspirates, lung tissue, and feces. Collection and storage methods of biological samples are known to those of skill in the art. Biological samples can be processed (e.g., by nucleic acid extraction methods and/or kits known in the art) to release GBS nucleic acid or in some cases, the biological sample can be contacted directly with the PCR reaction components and the appropriate oligonucleotides.

Biological samples can be cultured in a medium suitable for growth of GBS. The culture media then can be assayed for the presence or absence of GBS using the methods of the invention as described herein. For example, samples arriving at a clinical laboratory for detection of GBS using the methods of the invention can be in the form of a liquid culture that had been inoculated with a biological sample from an individual.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the pts probes from the pts amplification product can confirm the presence or absence of GBS in the sample.

Within each thermocycler run, control samples are cycled as well. Positive control samples can amplify GBS nucleic acid control template (other than pts) using, for example, control primers and control probes. Positive control samples can also amplify, for example, a plasmid construct containing GBS pts nucleic acid molecules. Such a plasmid control can be amplified internally (e.g., within the sample) or in a separate sample run side-by-side with the patients' samples. Each thermocycler run should also include a negative control that, for example, lacks GBS template DNA. Such controls are indicators of the success or failure of the amplification, hybridization and/or FRET reaction. Therefore, control reactions can readily determine, for example, the ability of primers to anneal with sequence-specificity and to initiate elongation, as well as the ability of probes to hybridize with sequence-specificity and for FRET to occur.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are necessary for accuracy in a diagnostic laboratory handling clinical samples.

Conventional PCR methods in conjunction with FRET technology can be used to practice the methods of the invention. In one embodiment, a LightCycler™ instrument is used. A detailed description of the LightCycler™ System and real-time and on-line monitoring of PCR can be found at biochem.roche.com/lightcycler on the World Wide Web. The following patent applications describe real-time PCR as used in the LightCycler™ technology: WO 97/46707, WO 97/46714 and WO 97/46712. The LightCycler™ instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LightCycler™ thermal chamber. Addition of selected fluorescent dyes to the reaction components allows the PCR to be monitored in real time and on-line. Furthermore, the cuvettes serve as an optical element for signal collection (similar to glass fiber optics), concentrating the signal at the tip of the cuvette. The effect is efficient illumination and fluorescent monitoring of microvolume samples.

The LightCycler™ carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorometer, as part of the LightCycler™ apparatus, houses the light source. The emitted light is filtered and focused by an epi-illumination lens onto the top of the cuvette. Fluorescent light emitted from the sample is then focused by the same lens, passed through a dichroic mirror, filtered appropriately, and focused onto data-collecting photohybrids. The optical unit currently available in the LightCycler™ instrument (Roche Molecular Biochemicals, Catalog No. 2 011 468) includes three band-pass filters (530 nm, 640 nm, and 710 nm), providing three-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LightCycler™ can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBRGreenI® or SYBRGold® (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

As described herein, amplification products also can be detected using labeled hybridization probes that take advantage of FRET technology. A common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler™ Instrument. During FRET, the fluorescein transfers its energy to an acceptor fluorescent moiety such as LightCycler™-Red 640 (LC™-Red 640) or LightCycler™-Red 705 (LC™-Red 705). The acceptor fluorescent moiety then emits light of a longer wavelength, which is detected by the optical detection system of the LightCycler™ instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of GBS genomes).

Another FRET format utilizes TaqMan® technology to detect the presence or absence of an amplification product, and hence, the presence or absence of GBS. TaqMan® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TagMan® technology, and is suitable for performing the methods described herein for detecting GBS. Information on PCR amplification and detection using an ABI PRISM® 770 system can be found at appliedbiosystems.com/products on the World Wide Web.

Molecular beacons in conjunction with FRET also can be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

It is understood that the present invention is not limited by the configuration of one or more commercially available instruments.

Articles of Manufacture

The invention further provides for articles of manufacture to detect GBS. An article of manufacture according to the present invention can include primers and probes used to detect GBS, together with suitable packaging materials. Representative primers and probes for detection of GBS are capable of hybridizing to GBS pts nucleic acid molecules. Methods of designing primers and probes are disclosed herein, and representative examples of primers and probes that amplify and hybridize to GBS pts nucleic acid molecules are provided.

Articles of manufacture of the invention also can include one or more fluorescent moieties for labeling the probes or, alternatively, the probes supplied with the kit can be labeled. For example, an article of manufacture may include a donor fluorescent moiety for labeling one of the pts probes and an acceptor fluorescent moiety for labeling the other pts probe, respectively. Examples of suitable FRET donor fluorescent moieties and corresponding acceptor fluorescent moieties are provided above.

Articles of manufacture of the invention also can contain a package insert or package label having instructions thereon for using the pts primers and probes to detect GBS in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims.

EXAMPLES

Example 1

LightCycler Detection of Group B *Streptococcus*

A LightCycler assay was used to detect group B *streptococcus* (GBS) bacterial pathogens from vaginal/anal swabs. A conserved region of the phosphotransferase gene (pts) of GBS was used as a target for the PCR assay detection.

The primer sequences were as follows: primer 1: 5'-TGA GAA GGC AGT AGA AAG CTT AG-3' (SEQ ID NO:1); and primer 2: 5'-TGC ATG TAT GGG TTA TCT TCC-3' (SEQ ID NO:2). The probe sequences and labels were as follows: probe 1: 5'-CAA ATT AAA GAG ACT ATT CGT GCA A-fluorescein-3' (SEQ ID NO:3); and probe 2: 5'-LC-Red640-CAA GTA AAT GCA GAA ACA GG-phosphate-3' (SEQ ID NO:4).

Primers were adjusted to 50 µM by measuring the $A_{260}$ of a 1/50 dilution (196 µl water+4 µl, Dilution Factor (DF)=50). The concentration was estimated by the following formula:

(µM found/50)× µl remaining)– µl remaining=water to add

Probes were dissolved in TE' to a concentration of 20 µM (supplied with the probes and resuspended according to manufacturer's instructions). The concentration of oligonucleotides and dye was double checked by UV absorption using the following equations from *Biochemica*, 1999, 1:5-8:

$$[dye] = \frac{A_{dye}}{E_{dye}}$$

$$[oligo] = \frac{A_{260} - \left(A_{260} \times \frac{E_{260(dye)}}{E_{dye}}\right)}{\frac{10^6}{nmol/A_{260}}}$$

| | Absorbance | | | Emission |
|---|---|---|---|---|
| Dye | Abs max (nm) | $E_{dye}$ (M$^{-1}$cm$^{-1}$) | $E_{260(dye)}$ (M$^{-1}$cm$^{-1}$) | Max (nm) |
| Fluorescein | 494 | 68,000 | 2,000 | 524 |
| LC Red 640 | 622 | 110,000 | 31,000 | 638 |

Table 1 shows the PCR Reaction Mix.

TABLE 1

| Ingredient | Stock Concentration | µl |
|---|---|---|
| Water | | 11 |
| MgCl$_2$ | 50 mM | 1.2 |
| LC-FS-DNA MHP* | 10X | 2 |
| Primer 1 | 25 mM | 0.24 |
| Primer 2 | 25 mM | 0.24 |
| Fluorescein Probe | 20 µM | 0.2 |
| Red640 Probe | 20 µM | 0.2 |
| Total Volume | | 15 |

*LC-FS-DNA MHP = LightCycler FastStart DNA Master Hybridization Probes (Roche, Catalog No. 3003248)

5 µl of the swab sample was mixed with 15 µl of the PCR Reaction Mix and added to the LightCycler cuvette for thermocycling. The samples were PCR amplified and the products were detected in a LightCycler instrument (Roche Applied Science, catalog 2011468). The PCR cycling procedure used is shown in Table 2.

TABLE 2

| PCR program | Cycles | Hold Time (seconds) | Temperature (° C.) | Slope (° C./sec) | Signal acquisition |
|---|---|---|---|---|---|
| Initial | 1 | 600 | 95 | 20 | None |
| PCR | 45 | 10 | 95 | 20 | None |
| | | 15 | 55 | 20 | Single |
| | | 15 | 72 | 20 | None |
| Melting | 1 | 0 | 95 | 20 | None |
| curve | | 20 | 59 | 20 | None |
| analysis | | 20 | 45 | 0.2 | None |
| | | 0 | 85 | 0.2 | Continuous |
| Cool | 1 | 10 | 40 | 20 | None |

The signal detected in the 640 nm channel of the LightCycler instrument was analyzed. A melting curve analysis, performed after the PCR amplification, was used to confirm detection of GBS. GBS positive samples demonstrate a Tm of 58° C. plus or minus 2° C., and were compared directly to the positive control. Negative samples had no melting curve.

Plasmid controls were produced by cloning the pts product amplified by the pts primers into a plasmid (TA Cloning® Kit, Invitrogen, Carlsbad, Calif.). The plasmid containing the target insert was used to determine the analytical sensitivity of the assays. Plasmid concentration or the copy number of the gene target insert was determined with the following formula:

DS DNA, $A_{260}$ to molecules/μl

Given:
1. ($A_{260}$ × Dilution Factor)/20=mg/ml=μg/μl DS DNA
   1 $A_{260}$=50 μg/ml
   1 $A_{260}$ (50)=μg/ml
   1 $A_{260}$ (50)/1000=μg/μl
2. (6.02×10$^{23}$ molecules/mole)/(10$^{12}$ pmole/mole)=6.02× 10$^{11}$ molecules/pmole
3. Base pairs of DNA in molecule=N Then:

$(A_{260} \times DF)/20$ μg/μl×10$^6$ pg/μg×1 pmol/660 pg×1/N× 6.02×10$^{11}$ molecules/pmole=molecules/μl Shortcut calculation:

$((A_{260} \times DF)/20) \times (9.12 \times 10^{14}/N)$=molecules/μl

Example 2

Specificity of LightCycler Assay of GBS

DNA extracted from cultures of a variety of different organisms were used to determine if the GBS assay would cross-react with non-GBS organisms. Organisms similar to GBS were tested as well as organisms commonly found in a vaginal or anal swab sample were tested. Table 3 shows the similar organisms tested and the results. Table 4 shows the other specimens tested and those results.

TABLE 3

| | Lancefield | Source | | |
|---|---|---|---|---|
| Organism | Group | ATCC | Other | LC assay |
| S. pyogenes | A | 19615 | | Neg |
| S. agalactiae | B | | CAPXL36 | Pos |
| S. suis | | 43765 | | Neg |
| L. lactis | | 19435 | | Neg |
| S. equi ss equi | C | 33398 | | Neg 51° C. melt |
| S. uberis | | 19436 | | Neg |
| S. canis | G | 43496 | | Neg 51° C. melt |
| E. faecium | | | CAP-D-18-83 | Neg |

TABLE 3-continued

| | Lancefield | Source | | |
|---|---|---|---|---|
| Organism | Group | ATCC | Other | LC assay |
| S. bovis | | | CAP-D-16-83 | Neg |
| E. faecalis | | 29212 | | Neg |
| S. dysgalactiae | C | 43078 | | Neg 51° C. melt |
| S. salivarius | | 7073 | | Neg |
| S. equinus | | 9812 | | Neg |
| S. pneumoniae | | 49619 | | Neg |
| S. porciuns | | 43138 | | Neg |
| S. iniae | | 29178 | | Neg |
| S. anginosus | | 33397 | | Neg |
| S. MG-intermedius | | | CAP-D-17-87 | Neg |
| Group F strep | F | | SCB-21-89 | Neg |
| S. sanguis | | | SCB-33-83 | Neg |
| S. mitis | | 49456 | | Neg |
| S. oralis | | 35037 | | Neg |
| S. gordonii | | 10558 | | Neg |
| S. mutans | | | QC strain - Mayo | Neg |
| S. intermdius | | 27335 | | Neg |
| S. anginosus | | 33397 | | Neg |

TABLE 4

| Respiratory | | |
|---|---|---|
| Organism | Source | LC result |
| Acinetobacter bauminii | patient isolate | Neg |
| Acinetobacter lwoffii | QC Strain | Neg |
| Aeromonas hydrophila | CAP-D-1-82 | Neg |
| Bordetella bronchioseptica | patient isolate | Neg |
| Bordetella parapertussis | ATCC 15311 | Neg |
| Campylobacter jejuni | CDC-AB2-C15-82 | Neg |
| Corynebacterium (Archanobacterium) haemolyticum | patient isolate | Neg |
| Corynebacterium diptheriae | SCB-25-86 | Neg |
| Corynebacterium pseudodiptheriae | NY-4-88 | Neg |
| Escherichia coli | patient isolate | Neg |
| Haemophilus influenza | ATCC 49766 | Neg |
| Human DNA | MRC-5 cells | Neg |
| Klebsiella oxytoca | patient isolate | Neg |
| Klebsiella pneumoniae | patient isolate | Neg |
| Legionella jordanis | ATCC 33623 | Neg |
| Legionella pneumophila | ATCC 33152 | Neg |
| Listeria monocytogenes | patient isolate | Neg |
| Moraxella catarrhalis | patient isolate | Neg |
| Morganella morganii | CAP-D-5-79 | Neg |
| Mycoplasma pneumoniae | patient isolate | Neg |
| Neiserria gonorrheae | patient isolate | Neg |
| Neiserria meningitides | patient isolate | Neg |
| Proteus vulgaris | patient isolate | Neg |
| Pseudomonas cepacia | patient isolate | Neg |
| Pseudomonas fluorescens | patient isolate | Neg |
| Staphylococcus aureus | ATCC 25923 | Neg |
| Staphylococcus epidermidis | patient isolate | Neg |
| Stenotrophomonas maltophilia | SOB-33-77 | Neg |
| Citrobacter freundii | patient isolate | Neg |
| Bordetella bronchioseptica | ATCC 19395 | Neg |

| Stool panel | | |
|---|---|---|
| Organism | source | LC assay |
| Actinomyces pyogenes | clinical | Neg |
| Aeromonas hydrophila | CAP-D-1-82 | Neg |
| Bacteroides distasonis | ATCC 8503 | Neg |
| Bacteroides fragilis | ATCC 25285 | Neg |
| Bacteroides thetaiotaomicron | ATCC 29741 | Neg |
| Bacteroides vulgatus | ATCC 29327 | Neg |
| Citrobacter freundii | clinical | Neg |

TABLE 4-continued

| | | |
|---|---|---|
| Clostridium perfringens | ATCC 13124, Cl417 | Neg |
| E. coli O70:K:H42 | ATCC 23533 | Neg |
| Enterobacter cloacae | clinical-1004 | Neg |
| Enterococcus faecalis | clinical V583 | Neg |
| Enterococcus faecium | clinical B7641 | Neg |
| Escherichia hermanii | clinical | Neg |
| Escherichia vulneris | clinical | Neg |
| Eubacterium lentum | ATCC 43055 | Neg |
| Fusobacterium nucleatum | ATCC 25559 | Neg |
| Klebsiella pneumoniae | ATCC 700603 | Neg |
| Proteus mirabilis | QC strain | Neg |
| Pseudomonas aeruginosa | ATCC 27853 | Neg |

| Genital-Urinary panel | | |
|---|---|---|
| Organism | Source | LC Result |
| Acinetobacter lwoffi | clinical | Neg |
| Candida albicans | clinical | Neg |
| Neisseria gonorrheae | clinical | Neg |
| Corynebacterium pseudotubercuolsis | ATCC 10700 | Neg |
| Gardnerella vaginalis | clinical | Neg |
| Mobiluncus curtissi | clinical | Neg |
| Mycoplasma | clinical | Neg |
| Neisseria lactamica | clinical | Neg |
| Peptostreptococcus magnus | clinical | Neg |
| Porphyromonas gingivalis | clinical | Neg |
| Prevotella bivia | clinical | Neg |
| Ureoplasma | clinical | Neg |

Example 3

Analytical Sensitivity of the LightCycler Assay

As few as 5 copies of GBS target DNA per reaction were detected by the GBS LightCycler assay.

Example 4

Clinical Sensitivity of the LightCycler Assay

Prior to the LightCycler technology, the gold standard for detection of GBS was culture. Culture results from vaginal/anal swab specimens from women collected during the 35 to 37 week of pregnancy were compared to the LightCycler GBS assay.

| | Culture | | |
|---|---|---|---|
| LC | Present | Absent | Totals |
| Positive | 37 | 4 | 41 |
| Negative | 0 | 134 | 134 |
| Totals | 37 | 138 | 175 |

The results below were calculated using StatsDirect version 1.9.15 software (StatsDirect Ltd, Cheshire, UK) and include 95% confidence intervals (shown in parentheses). An explanation of the values shown below and how those values are calculated can be found at musc.edu/dc/icrebm/sensitivity.html on the World Wide Web.

| | | Disease | |
|---|---|---|---|
| | | Present | Absent |
| Test | + | a (true) | b (false) |
| | − | c (false) | d (true) |

Prevalence (percent of affected patients tested; [a+c/d]):
  21.14% (15.34% to 27.95%)
Positive predictive value (percent of patients with a positive test having the disease; [a/a+b]):
  90.24% (76.87% to 97.28%)
Negative predictive value (percent of patients with a negative test without the disease; [d/d+c]):
  100% (97.28% to *%)
Sensitivity (true positives detected per total affected patients tested; [a/a+c]):
  100% (90.51% to *%)
Specificity (true negatives per unaffected patients tested; [d/b+d]):
  97.1% (92.74% to 99.2%)

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting the presence or absence of GBS in a biological sample from an individual, said method comprising:

performing at least one cycling step, wherein a cycling step comprises an amplifying step and a hybridizing step, wherein said amplifying step comprises contacting said sample with a pair of pts primers to produce a pts amplification product if a GBS pts nucleic acid molecule is present in said sample, wherein said pair of pts primers comprise a first pts primer and a second pts primer, wherein said first pts primer consists of the sequence 5'-TGA GAA GGC AGT AGA AAG CTT AG-3' (SEQ ID NO:1), and wherein said second pts primer consists of the sequence 5'-TGC ATG TAT GGG TTA TCT TCC-3' (SEQ ID NO:2), wherein said hybridizing step comprises contacting said sample with a pts probe, wherein said pts probe is selected from a sequence consisting of 5'-CAA ATT AAA GAG ACT ATT CGT GCA A-3' (SEQ ID NO:3), a sequence consisting of 5'-CAA GTA AAT GCA GAA ACA GG-3' (SEQ ID NO:4), and a sequence that permits secondary structure formation, wherein the pts probe is labeled with a donor fluorescent moiety and a corresponding acceptor fluorescent moiety; and detecting the presence or absence of fluorescence resonance energy transfer (FRET) between said donor fluorescent moiety and said acceptor fluorescent moiety of said pts probe, wherein the presence or absence of fluorescence is indicative of the presence or absence of GBS in said sample.

2. The method of claim 1, wherein said amplification employs a polymerase enzyme having 5' to 3' exonuclease activity.

3. The method of claim 2, wherein said donor and corresponding acceptor fluorescent moieties are within no more than 5 nucleotides of each other on said probe.

4. The method of claim 3, wherein said corresponding acceptor fluorescent moiety is a quencher.

5. The method of claim 1, wherein said corresponding acceptor fluorescent moiety is a quencher.

6. The method of claim 1, wherein said cycling step is performed on a control sample.

7. The method of claim 6, wherein said control sample comprises said GBS pts nucleic acid molecule.

8. The method of claim 1, wherein said cycling step uses a pair of control primers and a control probe, wherein said control primers and said control probe are other than said pts primers and said pts probe, wherein a control amplification product is produced if control template is present in said sample, wherein said control probe hybridize to said control amplification product.

9. The method of claim 1, wherein said detecting step is performed after each cycling step.

10. The method of claim 1, wherein said detecting step is performed in real time.

11. The method of claim 1, further comprising preventing amplification of a contaminant nucleic acid.

12. The method of claim 11, wherein said preventing comprises performing said amplifying step in the presence of uracil.

13. The method of claim 12, wherein said preventing further comprises treating said biological sample with uracil-DNA glycosylase prior to a first amplification step.

14. The method of claim 1, wherein said biological sample is selected from the group consisting of anal and/or vaginal swabs.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide

<400> SEQUENCE: 1
tgagaaggca gtagaaagct tag          23

<210> SEQ ID NO 2
<211> LENGTH: 21
<212> TYPE: DNA
<213> ORGANISM: Artificial Sequence

```
<220> FEATURE:
<223> OTHER INFORMATION: Oligonucleotide

<400> SEQUENCE: 2
tgcatgtatg ggttatcttc c                                          21

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide

<400> SEQUENCE: 3
caaattaaag agactattcg tgcaa                                      25

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
caagtaaatg cagaaacagg                                            20
```